United States Patent [19]

Jones, Sr.

[11] 4,041,950

[45] Aug. 16, 1977

[54] FLUFFED PULP URINE TRAP DIAPER

[76] Inventor: John Leslie Jones, Sr., 1070 Glen Oaks Blvd., Pasadena, Calif. 91105

[21] Appl. No.: 706,762

[22] Filed: July 23, 1976

[51] Int. Cl.² .................... A61F 13/16; A61F 13/18
[52] U.S. Cl. ................................. 128/287; 128/284; 128/290 P; 128/290 R; 128/296
[58] Field of Search ............... 128/284, 287, 290 R, 128/290 P, 296

[56] References Cited

U.S. PATENT DOCUMENTS

| 2,788,003 | 4/1957 | Morin | 128/284 |
|---|---|---|---|
| 2,895,477 | 7/1959 | Bernard | 128/284 |
| 3,211,147 | 10/1965 | Pherson et al. | 128/284 |
| 3,481,337 | 12/1969 | Ruffo | 128/284 |
| 3,650,273 | 3/1972 | Schaar | 128/287 |
| 3,658,063 | 4/1972 | Schaar | 128/287 |
| 3,731,688 | 5/1973 | Litt | 128/287 |
| 3,765,418 | 10/1973 | Jones, Sr. | 128/287 |
| 3,968,798 | 7/1976 | Hokanson | 128/284 |

Primary Examiner—Aldrich F. Medbery
Attorney, Agent, or Firm—J. L. Jones, Sr.

[57] ABSTRACT

An infant diaper has a coherent absorbent pad with a pair of exterior longitudinal pad margins oppositely disposed to each other. The absorbent pad area has a central pad area in combination with an opposed pair of absorbent border pad areas, each one of the opposed border pad areas has one longitudinal boundary margin adjacently coextensive with one longitudinal boundary margin of the central pad area. A central optimum pad area can have a discrete weight greater than each one of the border pad areas. A pair of parallel, narrow width pleats are disposed the full longitudinal pad axis length. Each one of the pair of pleats can be formed of the central pad area and are disposed on the same first face of the central pad area adjacent to the longitudinal boundary margin of the central pad area. Each one of the pleats can have a pleat apex disposed nearer or further from the central longitudinal pad axis than the corresponding companion pleat base fold. A thin, flexible, fluid impermeable membrane is contiguously disposed coextensive with the second face of the absorbent pad area opposite the first pad face, specifically excluding the side width values of the pair of narrow width pleat sides. The membrane also forms each one of a pair of opposed longitudinal border seals.

12 Claims, 7 Drawing Figures

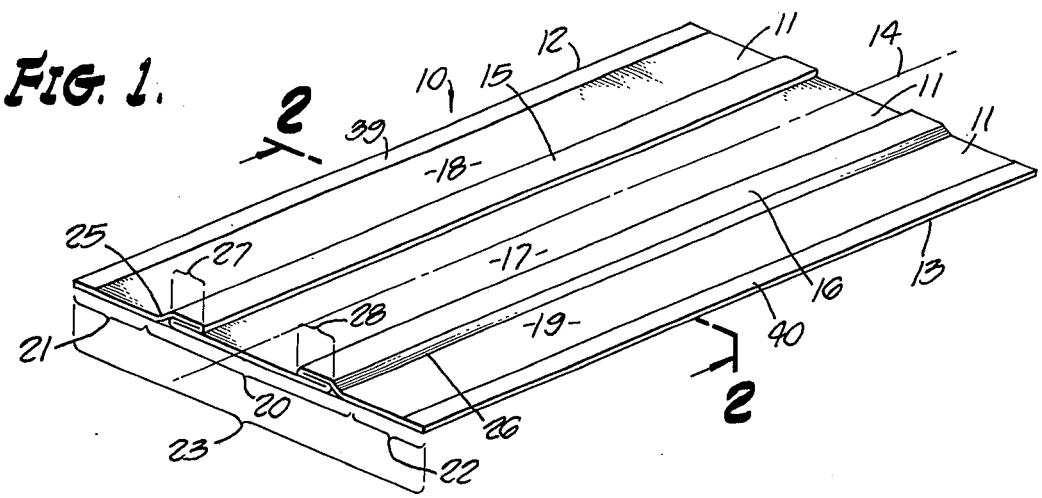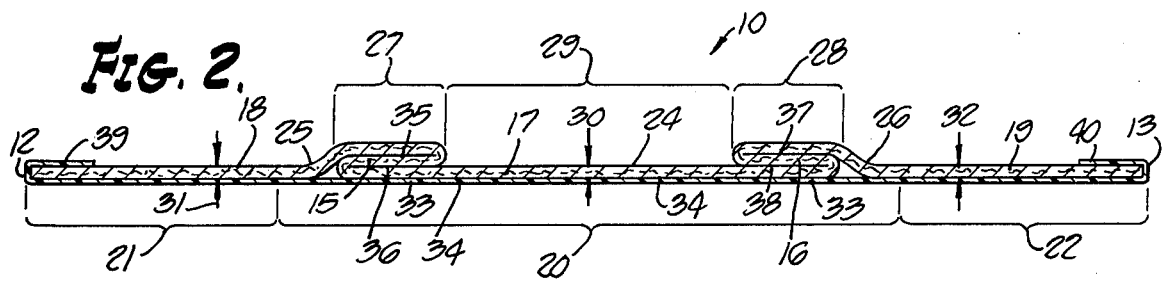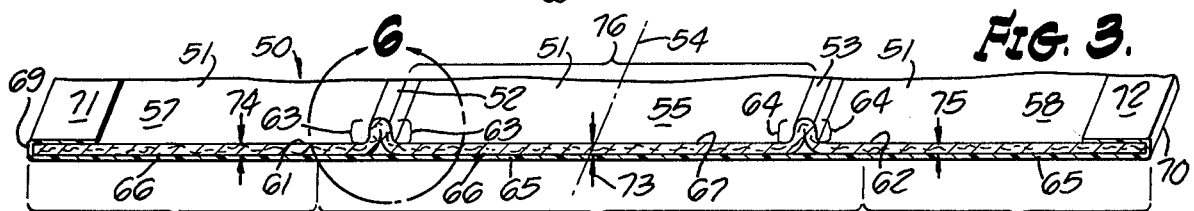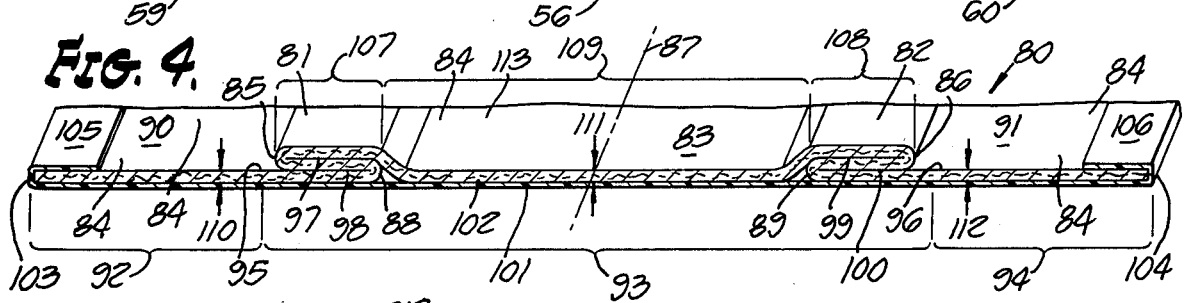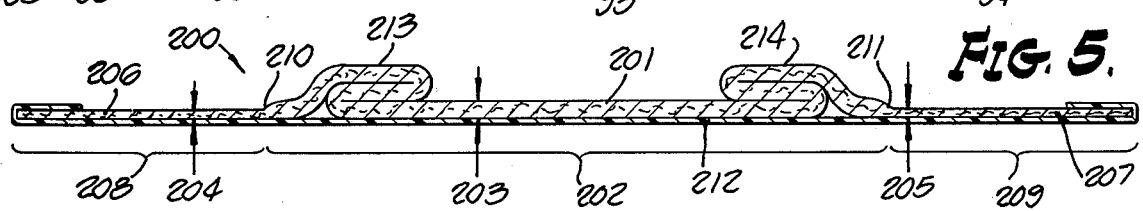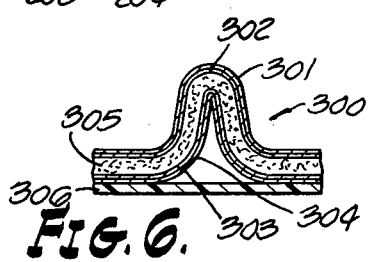

FLUFFED PULP URINE TRAP DIAPER

BACKGROUND OF THE INVENTION

The infant diaper of this invention is classified in Class 128, and sub-classes 287 and 284.

SUMMARY OF THE INVENTION

An infant diaper has a rectangular coherent absorbent pad area formed of fluffed wood pulp and absorbent cellulose sheeting, the pad area having a pair of exterior longitudinal pad margins oppositely disposed to each other, a central longitudinal pad axis and a total pad width axis normal to the longitudinal axis. A pair of absorbent opposed border pad areas and one central pad area, in combination and disposed parallel together, form the absorbent pad area. Each one of the border pad areas has a longitudinal boundary margin adjacently coextensive with the central pad area longitudinal boundary margin. Each one of the pair of border pad areas and the central pad area can have different discrete weight concentrations of selected fluffed cellulose pulp and cellulose sheeting per unit of pad area. A pair of narrow width, single pleats are disposed parallel to the full longitudinal pad length. Each one of the pair of pleats can be formed of the central pad area or of the adjacent border area and disposed on the first face of the pad area adjacent to the longitudinal boundary margin of the central pad area. Each one of the pleats can be folded flat and have a pleat apex which can be disposed nearer or further from the central longitudinal pad axis than the corresponding companion pleat base fold. A major proportion of the central pad width is free of coverage by the pair of narrow pleats. The total absorbent pad width axis value specifically excludes the values of the pairs of narrow pleat width sides. A thin, flexible, waste fluid impermeable membrane is contiguously disposed coextensive with the second face of the absorbent pad area, opposite the first pad face, the membrane area specifically excluding contact with the side width values of the pair of narrow width pleat sides. The second face of the pad area has the aforesaid total pad width axis value and the longitudinal pad length, and the membrane is folded over and forming each one of a pair of opposed longitudinal border seals on the pair of longitudinal diaper pad margins.

The pair of oppositely disposed pleats and the central pad area between the pair of pleats, together provide an excreta channel pad area in the infant diaper absorbtion pad. During the few seconds required for absoption of urine, the channel pad area contains the urine, preventing the waste urine and feces from soiling the infant's other clothes, crib sheets and covers.

Included in the objects of this invention are:

To provide an effective excreta channel pad area trapping means for collecting infant urine and feces in the central absorbent pad area of a disposable infant diaper.

To provide an improved urine collecting means in the wood pulp absorbent pad of an infant disposable diaper.

To provide an optimum profile absorbent pad of wood pulp having an improved urine collection means incorporated in an infant disposable diaper.

To provide an optimum profile infant disposable diaper having improved urine flow control means, utilizing fluffed wood pulp and cellulose paper sheeting in the absorbent pad of the diaper.

Further objects and advantages of this invention will become apparent in the following description, to be read in conjunction with the accompanying drawing.

BRIEF DESCRIPTION OF THE DRAWINGS

FIG. 1 is a perspective full view of an infant diaper illustrating the pair of flat-folded pleats disposed on the first face of the absorbent pad area, providing an excreta channel pad area.

FIG. 2 is an elevational sectional view through 2—2 of FIG. 1.

FIG. 3 is a partial perspective view of a further infant diaper improvement, incorporating a sectional view of free standing pleats in the central pad area, providing another excreta channel pad area.

FIG. 4 is a partial perspective view and a sectional view of the central pad area incorporating a pair of pleats folded with the pleat apexes pointing to the pair of exterior diaper margins.

FIG. 5 is a sectional view of another diaper modification incorporating the optimum profile in the central absorbent pad area.

FIG. 6 is an enlarged fragmentary sectional view illustrating the detailed structure of the free-standing pleats shown in FIG. 3.

FIG. 7 is a fragmentary sectional view of the central absorbent pad section of FIG. 2 after absorption of urine.

DESCRIPTION OF THE PREFERRED EMBODIMENT OF THE INVENTION

Referring to FIGS. 1 and 2 together in detail, the rectangular area infant diaper 10 is first shown in planar perspective view, having an absorbent pad 11 formed of fluffed wood pulp and absorbent cellulose sheeting. Fluffed cellulose pulp is the variety of typically bleached cellulose wood pulp which has been fragmented into a low density cellulose composition of short wood fibers. The fluff pulp is typically produced by breaking up bleached alpha cellulose sheets in a hammer mill. The shredded wood fibers are then spread into a wood pulp pad and compacted as required. The absorbent pad 11 can have a typical absorbent cellulose paper sheet exterior forming an envelope, and an interior absorbent pad of fluffed cellulose pulp, providing the required weight of absorbent pulp per unit of area. An equivalent absorbent pad 11 can have an absorbent, cellulose paper sheet exterior and alternate layers of fluffed cellulose pulp and of cellulose paper sheets, as are required to provide the necessary weight of absorbent cellulose per unit of area for the absorption of waste fluid. The absorbent pad 11 can also include a conventional porous scrim type exterior cover sheet.

The diaper 10 has a pair of exterior longitudinal diaper pad margins 12 and 13, together with a central longitudinal pad axis 14, and a total diaper width 23 which is measured normal to the pad axis 14. A pair of narrow width, flat-folded pad pleats 15 and 16 are oppositely spaced and disposed parallel on the pad 11 along the full length of the longitudinal pad axis 14. A pair of absorbent border pad areas 18 and 19, together with the central pad area 17, combine to form the total absorbent pad area 11. The border pad area 18 has a border width 21, the border pad area 19 has the border width 22, and the central pad area 17 has the pad width 20. The three pad component areas 17, 18 and 19 combine to form the total pad area 11, having a pad width of 20, 21 and 22 which is equivalent to the total pad width 23.

Each one of the pad pleats 15 and 16 can be formed of the central pad area 17 or can alternatively be formed of the border pad areas 18 and 19. The pleats 15 and 16 are disposed on the first face 24 of the pad 11. A pair of longitudinal boundary margins 25 and 26 of the central pad area 17, also provide the coextensive longitudinal boundary margin of the respective corresponding border pad areas 18 and 19. The flat-folded pleats 15 and 16 have the respective narrow widths 27 and 28. A proportionally large width 29 of the central pad 17 is free of coverage by the pleats 15 and 16 on the first pad face 24. An excreta channel pad area is provided by pleats 15 and 16 together with central pad area 17. The thickness of the central pad area 17 has a value 30, and the border pad areas 18 and 19 have the respective thicknesses of 31 and 32. Although the sectional view of FIG. 2 illustrates equal values of thicknesses 30, 31, 32, their thickness values can be different as will be discussed later.

The thin, flexible, fluid impermeable membrane 33 is disposed adjacently coextensive with the second face 34 of the absorbent pad 11, specifically excluding the side width values 35 and 36 of pleat 15 and excluding the side width values 37 and 38 of pleat 16. Thus the total diaper pad width 23 specifically excludes the side width values 35, 36, 37 and 38. The membrane 33 is coextensive with all of the second face pad width 23, and extends the complete longitudinal diaper length represented by the axis 14. The membrane 33 extends and overlaps over the pad 11 at the margins 12 and 13, having the pair of longitudinal border seals 39 and 40 disposed on the longitudinal diaper pad margins, sealed by utilizing known teachings.

Another modification of the pair of opposed pleats is illustrated in FIG. 3, wherein the diaper 50 is shown in partial perspective and sectional view having an absorbent pad 51, whose overall planar rectangular dimensional shape as to width and length is similar to pad 11, and to other conventional infant diapers. The absorbent pad 51 has a pair of low-height free standing pleats 52 and 53 oppositely disposed parallel along the entire longitudinal pad central axis 54 of the diaper length. Each one of the pair of pleats 52 and 53 are formed of the central pad area 55 whose pad width 56 is defined by the central bracket. The waste channel width 76 is also bracketed. The pair of border pad areas 57 and 58 have the respective border pad widths 59 and 60. The longitudinal boundary margins 61 and 62 respectively designate the adjacently coextensive common margins of the respective pairs of pads 55-57 and 55-58, extending coextensively the entire diaper length. Each one of the pleats 52 and 53 have the respective pleat side width values 63 and 64. The excreta channel pad area comprises pad area 55, and pleats 52 and 53 together.

A thin, flexible, waste fluid impermeable membrane 65 is disposed adjacently coextensive with the second face 66 of absorbent pad 51 opposite to the first face 67 of pad 51. The The membrane 65 is coextensive with the total diaper pad width axis value, which is the sum of widths 56, 59 and 60, and specifically excludes the pleat side width values 63 and 64. The membrane 65 also has a width value providing the overlap of the diaper margins 69 and 70, and providing the pair of opposed longitudinal border seals 71 and 72, which utilize known sealing teachings. The thickness 73 of the central pad area 55, the thickness 74 of the border pad area 57, and the thickness 76 of the border pad area 58 are illustrated as equivalent. As will be discussed later, the thicknesses 73, 74 and 75 also can be unequal, with a thickness 75 providing more fluffed pulp in central pad area 55, where the excretion action occurs.

In FIG. 4 the diaper 80 has a pair of oppositely parallel disposed flat-folded pleats 81 and 82, formed of the central pad area 83 of the absorbent pad 84. The diaper 80 has the overall planar dimensional shape similar to diaper 10. The pleats 81 and 82 have the length configuration on diaper 80 which is similar to diaper 10, and the pleat apexes 85 and 86 of the respective pleats 81 and 82 are disposed further from the central longitudinal pad axis 87 than the respective pleat base folds 88 and 89. The absorbent border pad areas 90 and 91 are disposed on each side of the central pad area 83. The respective pad areas 90, 83 and 91 each have the respective pad widths 92, 93 and 94. Thus, the border pad areas 90 and 91, together with central pad area 83, extend for the full diaper length, similar to the pad areas 17, 18 and 19 of pad 11. Again, the imaginary lines 95 and 96 extending the full diaper length, as in diaper 10, provide the respective longitudinal boundary margin of the adjacently coextensive pad pairs 90-83 and 91-83.

The pair of pleats 81 and 82 have the respective pleat side width values 97, 98 and 99, 100. The absorbent pad 84 has a total diaper pad width value of 92, plus 93, plus 94, and the total diaper pad width axis value specifically excludes the values of the pleat side width values 97, 98 and 99, 100. The thin, flexible, urine fluid impermeable membrane 101 is disposed contiguously coextensive with the second face 102 of the absorbent pad 84 for the length and width of the pad 84, specifically excluding the pleat side width values 97, 98 and 99, 100. The membrane 101 extends over the diaper pad exterior margins 103 and 104 and overlaps the margins to provide the respective longitudinal border seals 105 and 106. The narrow flat-folded pleats 81 and 82 have the respective pleat widths 107 and 108. The excreta channel pad area includes pad area 83 together with pleats 81 and 82, together providing a means for channeling infant excreta and retaining the urine and feces in the channel pad area, while the urine is being absorbed on the first face 113 of the pad 84. As in the diapers 10 and 50, the diaper 80 has the pad thicknesses 110, 111 and 112 corresponding to the respective border pad area 90, central pad area 83 and the border pad area 91. The illustrated values of 110, 111 and 112 are shown equivalent, but they can be different, preferably the thickness 111 can be greater than thicknesses 110 and 112.

Referring to FIG. 5, the cross sectional view of the diaper 200 illustrates a modification of the diaper 10 of FIGS. 1 and 2, wherein the central optimum pad area 201, with a central pad width 202, has a central thickness 203, which is greater than the border pad thicknesses 204 and 205. The border pads 206 and 207 have the respective pad widths 208 and 209. The respective coextensive longitudinal boundary margins 210 and 211 delineate the boundary of pad pairs 206-201 and 207-201. In general the values of the absorbent pad thicknesses 30, 31, 32 and 73, 74, 75, and 110, 111, 112, and 203, 204, 205 are adapted to those values of pad thicknesses required to contain and to absorb the excreted wastes. By providing the required central pad thickness of 30, 73, 111 and 203, the absorption of waste fluid in the fluffed pulp of the absorption pad can be maximized in the excreta channel pad areas. Thus, the amount of fluffed wood pulp and absorbent cellulose sheet can be minimized in the border area thicknesses 31, 32, and 204, 205, and the like. The configuration of the membrane 212 and the pleats 213 and 214 of diaper 200 are similar to those of diaper 10.

FIG. 6 illustrates in enlarged detail a typical cross sectional construction of the free-standing pleat 300 similar to the pair of pleats 52 and 53 of FIG. 3 in the section 6. The free-standing pleat 300 has two ply of absorbent cellulose sheet 301 and 302 exterior and two ply of cellulose sheets 303 and 304 interior, enveloping an interior fluffed wood pulp pad 305. The contiguous membrane 306 is shown to be excluded from penetration into the pleat 300. Other numbers of sheet ply can be utilized.

Basic to the invention is the provision of a pair of channel walls or dikes formed by the paired pleats 15, 16 of diaper 10, the paired pleats 52, 53 of diaper 50, the paired pleats 81, 82 of the diaper 80, and the paired pleats 213, 214 of diaper 200. The just listed above paired pleats and their respective enclosed pad areas provide the waste excreta channel pad areas between the respective pleat pairs typically utilizing the bracketed channel widths 29, 79, 109 and the like. Thus the waste excreted by the infant wearing the respective diaper typically flows into the respctive excreta channel pad areas. The urine, which requires a few seconds for absorption by the cellulosic pads 11, 51, and the like, is retains in the channel pad areas by the pleats until absorption occurs. The optimum central pad area can provide for the required placement of sufficient absorption fluffed cellulose pulp material in the waste channel to quickly absorb all the liquid.

Dimensionally, the narrow, flat-folded pleat pairs 15, 16 and 81, 82 and 213, 214, and the like can have the respective pleat widths 27, 28 and 107, 108, and the like, which can range in value from ¼ to 1 inch. The freestanding pleat pair 52, 53 and the like can have pleat side width values ranging substantially from ⅛ to ⅜ inch, or the like.

The pair of lateral pleats provide a means for securing the fluffed wood pulp in a restricted and fixed position in the waste excreta channel pad area. Thus it is possible to dispose an increased weight concentration of fluffed wood pulp in the channel pad area and to keep the wood pulp secured there. The pair of pleats provide an equivalent pair of lateral stress expansion joints in each diaper. Thus there is a much smaller probability of the splitting of the previous cover sheet or the layers of absorbent paper sheeting in the pad during the wearing of the diaper by a physically active infant.

Referring to FIG. 7, a fragmentary portion of the diaper 10 is illustrated, as modified by wetting the diaper with urine. The wet diaper 10′ is shown increased slightly in thickness 30′, and the pair of opposed wet pleats 15′ and 16′ lift upward slightly, providing a deeper waste channel for retaining later urine excretion.

The rectangular planar shape of the diapers disclosed in this invention provides good coverage of the torso and the thighs of the infant diaper wearer. Thus the diaper absorbent pad portions designated border pad areas can be wrapped around the infant thighs and can contain and absorb the urine and other excreta which escapes the waste channels. The improved containment and absorption of waste fluid by the improved diaper of this invention can prevent soiling of the crib sheets, blankets and clothes worn by the infant wearer. The permanent channel controlling the excreta flow cannot be destroyed by accidentally pulling out or stretching the pleats by the person fitting the diaper to the infant wearer.

Other modifications in the diaper of this invention can be made in the light of my teaching. It is understood that within the scope of the claims, the invention can be practiced otherwise than as specifically described.

I claim:

1. An infant diaper having a rectangular absorbent pad area formed of fluffed wood pulp and absorbent cellulose sheeting, aforesaid pad area having a pair of longitudinal pad margins oppositely disposed to each other, a central longitudinal pad axis, and a total pad width axis normal to said longitudinal pad axis, wherein the improvement combination comprises:

a pair of absorbent border pad areas and one central pad area together in combination form the aforesaid absorbent pad area, each one of said border pad areas having one longitudinal boundary margin adjacently coextensive with one central pad area longitudinal boundary margin, each one of said pair of border pad areas and said central pad area having a discrete weight concentration of fluffed cellulose pulp and cellulose sheeting per unit of each pad area;

a pair of narrow width pad pleats disposed parallel along the full longitudinal pad axis length, each one of said pair of pad pleats formed of said central pad area and disposed on the first face of said pad area adjacent to the longitudinal boundary margin of said central pad area, a major proportion of the central pad width being free of coverage by said pair of narrow pleats, the total absorbent pad width axis value having the value of the second face width of said absorbent pad area, excluding the side width values of the pair of narrow width pleat sides, said pair of pleats and the spaced pad area between said pleats together providing an excreta channel pad area; and, a thin, flexible, fluid impermeable membrane disposed adjacently co-extensive with said second face of said absorbent pad area, said membrane also forming each one of a pair of opposed longitudinal border seals disposed on said pair of longitudinal diaper pad margins.

2. In the combination set forth in claim 1, the further modification wherein the pair of narrow pleats have side width values ranging from ¼ to 1 inch.

3. In the combination set forth in claim 2, the further modification wherein the pair of pleat apexes are disposed nearer said central longitudinal diaper pad axis than the corresponding pair of pleat base folds.

4. In the combination set forth in claim 2, the further modification wherein the pair of pleat apexes are disposed further from said central longitudinal diaper pad axis than the corresponding pair of pleat base folds.

5. An infant diaper having a rectangular absorbent pad area formed of fluffed wood pulp and absorbent cellulose sheeting, aforesaid pad area having a pair of longitudinal pad margins oppositely disposed to each other, a central longitudinal pad axis, and a total pad width axis normal to said longitudinal pad axis, wherein the improvement combination comprises:

a pair of absorbent border pad areas and one central optimum pad area together in combination form the aforesaid absorbent pad area, each one of said border pad areas having one longitudinal boundary margin adjacently coextensive with one channel optimum pad area longitudinal boundary margin, each one of said pair of border pad areas and said central optimum pad area having a discrete weight concentration of fluffed cellulose pulp and cellulose sheeting per unit of pad area, said central optimum pad area having a greater discrete weight concentration of fluffed cellulose pulp than said pair of border pad areas;

a pair of narrow width pad pleats disposed parallel along the full longitudinal pad axis length, each one of said pair of pad pleats formed of said central optimum pad area and disposed on the first face of said central optimum pad area closely adjacent to the longitudinal boundary margin of said central optimum pad area, a major proportion of said central optimum pad width being free of coverage by said pair of narrow pleats, and the diaper total absorbent pad width axis value having the value of the second face width of said absorbent pad area, excluding the side width values of the pair of narrow width pleat sides, said pair of pleats and the spaced pad area between said pleats together providing an excreta channel pad area; and, a thin, flexible, fluid impermeable membrane disposed adjacently coextensive with said second face of said absorbent pad area, said membrane also forming each one of a pair of opposed longitudinal border seals disposed on said pair of longitudinal diaper pad margins.

6. In the combination set forth in claim 5, the further modification wherein the pair of narrow pleats have side width values ranging from ¼ to 1 inch.

7. In the combination set forth in claim 6, the further modification wherein the pair of pleat apexes are disposed nearer said central longitudinal diaper pad axis than the corresponding pair of pleat base folds.

8. In the combination set forth in claim 6, the further modification wherein the pair of pleat apexes are disposed further from said central longitudinal diaper pad axis than the corresponding pair of pleat base folds.

9. An infant diaper, having a rectangular absorbent pad area formed of fluffed wood pulp and absorbent cellulose sheeting, aforesaid pad area having a pair of longitudinal pad margins oppositely disposed to each other, a central longitudinal pad axis and a total pad width axis normal to said longitudinal pad axis, wherein the improvement combination comprises:

a pair of absorbent border pad areas and one central optimum pad area together in combination forming the aforesaid absorbent pad area, each one of said border pad areas having one longitudinal boundary margin adjacently coextensive with one central optimum pad area longitudinal boundary margin, each one of said pair of border pad areas and said central optimum pad area having a discrete weight concentration of selected fluffed cellulose pulp and absorbent cellulose sheeting per unit of pad area, said central optimum pad area having a greater discrete weight concentration of fluffed pulp than said pair of border pad areas;

a pair of narrow, pad pleats disposed parallel along the full longitudinal pad axis length, each one of said pair of pad pleats formed closely adjacent to said central optimum pad area and disposed on the first face of said absorbent pad area closely adjacent to the longitudinal boundary margin of said central optimum pad area, a major proportion of said central optimum pad area being free of coverage by said pair of narrow pleats, and the diaper total absorbent pad width axis value having the value of the second face width of said absorbent pad area, excluding the side width values of the pair of narrow width pleat sides, said pair of pleats and the pad area between said pleats together providing an excreta channel pad area; and, a thin, flexible, fluid impermeable membrane disposed adjacently co-extensive with said second face of said absorbent pad area, said membrane also forming each one of a pair of opposed longitudinal border seals disposed on said pair of longitudinal diaper pad margins.

10. In the combination set forth in claim 9, the further modification wherein the pair of narrow pleats have side width values ranging from ¼ to 1 inch.

11. In the combination set forth in claim 10, the further modification wherein the pair of pleat apexes are disposed nearer said central longitudinal diaper pad axis than the corresponding pair of pleat base folds.

12. In the combination set forth in claim 10, the further modification wherein the pair of pleat apexes are disposed further from said central longitudinal diaper pad axis than the corresponding pair of pleat base folds.

* * * * *